United States Patent [19]

Eibl et al.

[11] Patent Number: 5,714,370
[45] Date of Patent: Feb. 3, 1998

[54] THROMBIN AND METHOD OF PRODUCING THE SAME

[75] Inventors: Johann Eibl; Yendra Linnau, both of Vienna, Austria

[73] Assignee: Immuno Aktiengesellschaft, Vienna, Austria

[21] Appl. No.: 458,082

[22] Filed: Jun. 1, 1995

Related U.S. Application Data

[63] Continuation of Ser. No. 971,168, Nov. 4, 1992.

[30] Foreign Application Priority Data

Nov. 4, 1991 [AT] Austria .................. 2183/91

[51] Int. Cl.$^6$ .................................................. C12N 9/74
[52] U.S. Cl. .................. 435/214; 424/94.64; 424/529; 424/530; 530/384
[58] Field of Search ................ 424/94.64, 529, 424/530; 435/214; 530/384

[56] References Cited

U.S. PATENT DOCUMENTS

| | | | |
|---|---|---|---|
| 4,160,025 | 7/1979 | Eibl et al. | 530/384 |
| 4,272,523 | 6/1981 | Kotitschke et al. | 530/384 |
| 4,357,321 | 11/1982 | Thomes | 424/101 |
| 4,364,861 | 12/1982 | Mitra et al. | 260/112 B |
| 4,404,132 | 9/1983 | Mitra | 530/384 |
| 4,480,029 | 10/1984 | Dolana | 435/5 |
| 4,495,278 | 1/1985 | Thomas | 435/5 |
| 4,613,501 | 9/1986 | Horowitz | 435/238 |
| 4,640,834 | 2/1987 | Eibl et al. | 435/238 |
| 4,673,733 | 6/1987 | Chandra et al. | 530/344 |
| 4,764,369 | 8/1988 | Neurath et al. | 435/236 |
| 4,923,815 | 5/1990 | Tanaka et al. | 435/183 |
| 5,143,838 | 9/1992 | Kraus et al. | 435/214 |
| 5,151,355 | 9/1992 | Crowley et al. | 435/214 |
| 5,304,372 | 4/1994 | Michalski et al. | 435/214 |
| 5,354,682 | 10/1994 | Kingdon et al. | 435/214 |

FOREIGN PATENT DOCUMENTS

| | | |
|---|---|---|
| 350726 | 8/1976 | Austria . |
| 368883 | 7/1980 | Austria . |
| 385657 | 3/1984 | Austria . |
| 041173 | 5/1981 | European Pat. Off. . |
| 378798 | 12/1989 | European Pat. Off. . |
| 0439156 A1 | 7/1991 | European Pat. Off. . |
| 0 443 724 | 8/1991 | European Pat. Off. . |
| 3019612 | 5/1980 | Germany . |
| 3809991 | 3/1988 | Germany . |
| 3843126 | 6/1990 | Germany . |

OTHER PUBLICATIONS

Vinazzer, Thromb. Res., vol. 26, pp. 21–29, 1982.
Hoffman et al. Thromb. Res., vol. 20, pp. 623–631, 1980.
TS. Tsvetkov, et al., "A Method For Preparation Of Dry Thrombin For Topical Application," Cryobiology 21 (1984), pp. 661–663.
A.C. Guyton, *Textbook of Medical Physiology*, 6th ed., W.B. Saunders Co., 1981, pp. 92–98.
X.J. Yu et al., Journal of Chromatography, vol. 376, 1986, pp. 429–435.
G.D.O. Lowe et al., American Journal of Hospital Pharmacy, vol. 35, 1978, pp. 414–422.
A.M. Engel et al., The Journal of Biological Chemistry, vol. 246, No. 5, 1971, pp. 1213–1221.
B. Horowitz et al., "Transfusion", vol. 25, 1985, pp. 523–527.

*Primary Examiner*—Chhaya D. Sayala
*Attorney, Agent, or Firm*—Foley & Lardner

[57] ABSTRACT

A thrombin of human or animal origin is free of infectious agents and is produced by activation of prothrombin subjected to a heat treatment for the inactivation of infectious agents.

14 Claims, No Drawings

THROMBIN AND METHOD OF PRODUCING THE SAME

This application is a continuation of application Ser. No. 07/971,168, filed Nov. 4, 1992.

BACKGROUND OF THE INVENTION

The invention relates to a thrombin of human or animal origin as well as to a method of producing the same and its use.

The coagulation of blood involves a series of consecutive reactions, in which blood coagulation factors are activated and fibrin is finally formed by the action of activated prothrombin (thrombin) on fibrinogen. The transformation of prothrombin to thrombin is very slow with factor Xa and calcium alone. It is optimal only if a complex of several factors (prothrombinase complex) is present. In addition to factor Xa, factor V, phospholipids and calcium belong to this complex. Factor Xa proteolytically splits the prothrombin molecule (molecular weight 68 kD), thus generating the active enzyme thrombin (molecular weight 30 kD).

The plasma protease thrombin is a multi-functional enzyme not only having a coagulating activity due to the splitting of fibrinogen to fibrin, but also activating the coagulation factors V, VIII and XIII and its own proenzyme (prothrombin).

In therapy, thrombin is used alone or commonly with fibrinogen to stop bleedings or surgically for tissue adherence.

The activation of prothrombin via the prothrombinase complex is difficult to imitate ex situ, wherefor a number of experiments have been carried out to generate thrombin under the influence of proteases of human or animal origin. In doing so, it should be borne in mind that any contact of the product with human or animal substances is to be avoided due to the risk of contamination with infectious agents.

Assays on treating a prothrombin complex isolated from plasma with calcium ions alone as well as with calcium ions and a suspension containing bovine thromboplastin demonstrated that the treatment with calcium ions alone brings about a substantially lower yield and purity of the thrombin formed than does the treatment with calcium ions and thromboplastin (Cryobiology 21, 661–663 (1984)).

From DE-A - 38 43 126 it is known that thrombin can be obtained from plasma adsorbed on a matrix and treated with a prothrombin activator. Calcium ions, calcium ions and thromboplastin or factor Xa are cited as exemplary activators. During activation, all the biological co-factors adsorbed on the matrix are present.

When using plasmatic prothrombin for obtaining thrombin, there is the risk of contamination with infectious agents (e.g., hepatitis viruses; HIV). The risk of contamination is further increased when using known activation methods, which employ calcium $^{2+}$ ions and biological co-factors. The biological co-factors are a further source of contamination.

It is known that infectious agents in biological preparations can be reliably inactivated by a heat treatment, in particular in combination with a vapor treatment (AT-B - 385.657). Yet, it has been proved that thrombin, on account of its heat lability, must be heated in the presence of stabilizers (DE-A - 38 09 991) in order not to affect the activity of thrombin. However, the use of stabilizers is disputed, because during the heat treatment not only the thrombin activity is protected, but viruses are also stabilized.

SUMMARY OF THE INVENTION

It is the object of the invention to provide a virus-safe thrombin.

The virus-safe thrombin according to the invention is obtained from a virus-inactivated prothrombin-containing plasma fraction by activation exclusively by means of coagulatively active salts, such as, for instance, calcium, strontium or zinc ions. These salts promote the generation of thrombin from the corresponding coagulation factors.

The invention is based on the finding that infectious agents present in plasmatic prothrombin can be rendered innocuous by treatment of the prothrombin for virus inactivation without substantially affecting the biological activity of the thrombin obtained from prothrombin.

It has proved advantageous to generate the virus-safe thrombin from virus-inactivated prothrombin complex, in particular from virus-inactivated activated prothrombin complex. The activation of activated prothrombin complex by the addition of coagulatively active salts occurs at a surprisingly high reaction rate. Likewise, the yield of thrombin is optimized.

Surprisingly, it has been found that virus-safe thrombin can be generated by adding coagulatively active salts to a virus-inactivated plasma fraction containing prothrombin, such as a prothrombin complex or an activated prothrombin complex. The latter contains prothrombin and one or more activated coagulation factors. The generation of thrombin occurs without the addition of exogenous biological co-factors, such as factor V, factor Xa and phospholipids. Accordingly, a further source of potential contamination is avoided because generation of thrombin from prothrombin occurs without the additional presence of exogenous biological co-factors. The thrombin is virus-safe because a plasma fraction containing prothrombin was already virus-inactivated prior to the generation of the thrombin.

The production of virus-safe thrombin from FEIBA (Factor VIII Inhibitor Bypassing Activity) is particularly advantageous. An activated prothrombin complex or FEIBA can be obtained from a prothrombin complex by already known measures (AT-B - 350,726; AT-B - 368,883; EP-B - 0 041 173).

The invention also relates to a method of producing a virus-safe thrombin and is characterized by the combination of the following measures:

preparing an activated prothrombin complex from a prothrombin-containing plasma fraction, treating the activated prothrombin complex to inactivate infectious agents, and adding coagulatively active salts to the treated activated prothrombin complex in order to generate thrombin.

Advantageously, thrombin is further purified by ion exchange chromatography and/or affinity chromatography.

A virus-safe thrombin as described above is particularly suitable for the use in pharmaceutical preparations and for the production of diagnostics.

DETAILED DESCRIPTION OF PREFERRED EMBODIMENTS

The invention will be explained in more detail by way of the following examples, wherein Examples 3 and 4 relate to the further purification of the thrombin produced according to Example 1.

EXAMPLE 1

From 15 l human blood plasma cryoprecipitate poor, prothrombin (factor II) was bound to an anion exchanger (DEAE-SEPHADEX (dextran and epichlorohydrin)) together with coagulation factors VII, IX and X. After elution of the factor-II-containing fraction by means of an 0.5 molar NaCl solution, the salt concentration in this fraction was reduced to 0.15 mol/l by diafiltration and the fraction was subsequently freeze-dried.

In order to inactivate possibly present pathogens, this fraction was heated to 60° C. for 10 hours and to 80° C. for 1 hour according to AT-B - 385,657. The prothrombin activity was 5,250 U. The prothrombin was dissolved in a solution to 2.5 U/ml and slowly stirred with 2.5 mmol/l CaCl$_2$ at +30° C. and a pH of 7.0; after 80 minutes, the thrombin activity was determined (by means of chromogenic substrate Th-1 (Immuno)) to be 48 U per 1 U factor II.

By cooling to +4° C. and addition of ethylene diaminotetracetic acid (EDTA), the thrombin generation was stopped. The Ca-complex was eliminated by means of ultrafiltration/diafiltration using an ultrafiltration membrane (pore size: 10,000). Subsequently, the concentrate was finished to a pharmaceutical preparation.

EXAMPLE 2

20 ml of a FEIBA-containing solution (IMMUNO AG, Vienna) having a FEIB-activity of 966 units and 992 units factor II was diluted to 330 ml with an 0.9% NaCl solution and was slowly stirred with 2.75 mmol/l CaCl$_2$ at +30° C. After 90 minutes, the thrombin activity reached a maximum of 51 units per unit factor II. Activation was stopped by cooling of the solution to +4° C. and the addition of sodium citrate.

EXAMPLE 3

20,000 U thrombin produced according to Example 1 were adsorbed on a column of 20 ml S-SEPHAROSE (agarose) at a conductivity of 10.5 mS/cm and a pH of 6.0. Subsequently, it was washed with 140 ml of a 150 mmolar NaCl solution to eliminate the unbound proteins.

The thrombin-containing fraction was eluted with 100 ml of a 750 mmolar NaCl solution, concentrated, diafiltered and finally finished to a pharmaceutical preparation.

The yield of thrombin activity was more than 90%.

EXAMPLE 4

10,000 U thrombin produced according to Example 1 were applied on a column of 10 ml lysin-SEPHAROSE equilibrated with a 150 mmol sodium acetate solution, pH 6.7. The column was washed with the same buffer and the thrombin-containing fraction was eluted with a 300 mmolar lysin solution; the thrombin activity was 9,400 U and the specific activity was 1,850 U/mg protein.

What we claim is:

1. A pharmaceutical preparation comprising (i) a virus-safe human or animal thrombin and (ii) a coagulatively active salt, wherein the thrombin is obtained from a virus-inactivated prothrombin-containing plasma fraction by exclusive activation with the coagulatively active salt.

2. The preparation according to claim 1, wherein the fraction comprises a prothrombin complex.

3. The preparation according to claim 2, wherein the prothrombin complex is activated.

4. The preparation according to claim 1, wherein the fraction comprises Factor VIII Inhibitor Bypassing Activity (FEIBA).

5. A pharmaceutical preparation comprising a virus-safe human or animal thrombin, wherein the thrombin is obtained from a virus-inactivated prothrombin-containing fraction by exclusive activation with a coagulatively active salt.

6. The preparation according to claim 5, wherein the fraction comprises a prothrombin complex.

7. The preparation according to claim 6, wherein the prothrombin complex is activated.

8. The preparation according to claim 5, wherein the fraction comprises FEIBA.

9. A method for producing a pharmaceutical preparation comprising (i) virus-safe thrombin of human or animal origin and (ii) a coagulatively active salt, comprising (a) preparing an activated prothrombin complex from a prothrombin-containing plasma fraction;

(b) treating the activated prothrombin complex to inactivate contaminating viruses;

(c) contacting the treated activated prothrombin complex with a coagulatively active salt to generate thrombin; and (d) preparing the pharmaceutical preparation with the generated thrombin.

10. The method according to claim 9, wherein the preparing comprises purifying thrombin by at least one method selected from the group consisting of ion exchange chromatography and affinity chromatography.

11. A method for producing a preparation comprising (i) virus-safe human or animal thrombin and (ii) a coagulatively active salt, comprising (a) treating an activated human or animal prothrombin complex to inactivate contaminating viruses;

(b) contacting the treated activated prothrombin complex with a coagulatively active salt to generate virus-safe thrombin; and (c) formulating the preparation with the virus-safe thrombin from (b).

12. The method according to claim 11, further comprising purifying the generated virus-safe thrombin prior to (c) by at least one method selected from the group consisting of ion exchange chromatography and affinity chromatography to yield purified virus-safe thrombin.

13. A pharmaceutical preparation comprising a virus-safe human or animal thrombin, wherein the thrombin is obtained from a virus-inactivated prothrombin-containing fraction by the sole addition of a coagulatively active salt for activation.

14. The preparation according to claim 13, further comprising the coagulatively active salt.

* * * * *